(12) United States Patent
Biedermann et al.

(10) Patent No.: US 9,452,006 B2
(45) Date of Patent: Sep. 27, 2016

(54) POLYAXIAL BONE ANCHORING DEVICE WITH ENLARGED PIVOT ANGLE

(75) Inventors: Lutz Biedermann, VS-Villingen (DE); Timo Biedermann, Trossingen (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 233 days.

(21) Appl. No.: 13/610,045

(22) Filed: Sep. 11, 2012

(65) Prior Publication Data

US 2013/0096623 A1 Apr. 18, 2013

Related U.S. Application Data

(60) Provisional application No. 61/535,296, filed on Sep. 15, 2011.

(30) Foreign Application Priority Data

Sep. 15, 2011 (EP) ..................................... 11181514

(51) Int. Cl.
*A61B 17/70* (2006.01)
*A61B 17/84* (2006.01)
*A61B 17/88* (2006.01)

(52) U.S. Cl.
CPC ......... *A61B 17/844* (2013.01); *A61B 17/7037* (2013.01); *A61B 17/7038* (2013.01); *A61B 17/88* (2013.01)

(58) Field of Classification Search
CPC .............. A61B 17/70; A61B 17/7001; A61B 17/7032; A61B 17/7034; A61B 17/7035; A61B 17/7037; A61B 17/7038; A61B 17/704; A61B 17/7041; A61B 17/7043; A61B 17/7046

USPC ........... 606/60, 246–279, 300–320, 325–328
See application file for complete search history.

(56) References Cited

U.S. PATENT DOCUMENTS 1,346,673 A * 7/1920 Peterson ........................ 138/175
5,549,608 A * 8/1996 Errico et al. ................... 606/264
(Continued)

FOREIGN PATENT DOCUMENTS

| CN | 1371258 A | 9/2002 |
|---|---|---|
| CN | 1602171 A | 3/2005 |

(Continued)

OTHER PUBLICATIONS

Extended European Search Report for European Application No. 11181514.8, extended European Search Report dated Jan. 19, 2012 and mailed Jan. 30, 2012 (6 pgs.).

*Primary Examiner* — Lynnsy Summitt
(74) *Attorney, Agent, or Firm* — Lewis Roca Rothgerber Christie LLP

(57) ABSTRACT

A polyaxial bone anchoring device includes a bone anchoring element having a shank and a head, a receiving part including a rod receiving portion, and a head receiving portion having a first end and an open second end with a bounding edge, wherein the head receiving portion is configured to be rotatably connected to the rod receiving portion and is flexible for introduction and clamping of the head, and a locking ring configured to be mounted around the head receiving portion, wherein the head is insertable into the head receiving portion from the second end, is pivotable in the head receiving portion at a larger maximum pivot angle relative to the receiving part at a first location of the bounding edge, and can be locked at an angle relative to the receiving part by compressing the head receiving portion with the locking ring.

16 Claims, 7 Drawing Sheets

(56) References Cited

U.S. PATENT DOCUMENTS

| | | | | |
|---|---|---|---|---|
| 5,733,285 | A * | 3/1998 | Errico | A61B 17/7055 606/278 |
| 6,132,432 | A * | 10/2000 | Richelsoph | 606/278 |
| 6,736,820 | B2 | 5/2004 | Biedermann et al. | |
| 8,021,397 | B2 * | 9/2011 | Farris et al. | 606/269 |
| 8,100,946 | B2 * | 1/2012 | Strausbaugh et al. | 606/266 |
| 8,167,910 | B2 * | 5/2012 | Nilsson | 606/264 |
| 8,192,470 | B2 * | 6/2012 | Biedermann et al. | 606/265 |
| 8,197,519 | B2 * | 6/2012 | Schlaepfer et al. | 606/278 |
| 8,337,530 | B2 * | 12/2012 | Hestad et al. | 606/279 |
| 8,506,609 | B2 * | 8/2013 | Biedermann et al. | 606/306 |
| 8,506,610 | B2 * | 8/2013 | Biedermann et al. | 606/308 |
| 8,579,949 | B2 * | 11/2013 | Farris | A61B 17/7037 606/305 |
| 8,636,781 | B2 * | 1/2014 | Biedermann et al. | 606/306 |
| 8,636,782 | B2 * | 1/2014 | Biedermann et al. | 606/306 |
| 8,679,162 | B2 * | 3/2014 | Strausbaugh et al. | 606/266 |
| 8,685,064 | B2 * | 4/2014 | Hestad et al. | 606/266 |
| 8,764,805 | B2 * | 7/2014 | Biedermann | A61B 17/7037 606/269 |
| 8,881,358 | B2 * | 11/2014 | Biedermann | A61B 17/7037 29/238 |
| 9,066,759 | B2 * | 6/2015 | Biedermann | A61B 17/7037 |
| 9,173,684 | B2 * | 11/2015 | Biedermann | A61B 17/7037 |
| 2005/0080415 | A1 * | 4/2005 | Keyer | A61B 17/7038 606/278 |
| 2005/0080420 | A1 * | 4/2005 | Farris | A61B 17/7037 606/261 |
| 2005/0203515 | A1 * | 9/2005 | Doherty et al. | 606/61 |
| 2006/0200128 | A1 * | 9/2006 | Mueller | 606/61 |
| 2007/0118123 | A1 | 5/2007 | Strausbaugh et al. | |
| 2008/0015579 | A1 | 1/2008 | Whipple | |
| 2008/0177260 | A1 * | 7/2008 | McKinley et al. | 606/60 |
| 2008/0269742 | A1 * | 10/2008 | Levy et al. | 606/60 |
| 2009/0036934 | A1 | 2/2009 | Biedermann et al. | |
| 2010/0204735 | A1 * | 8/2010 | Gephart et al. | 606/264 |
| 2010/0305620 | A1 * | 12/2010 | Gotfried | 606/305 |
| 2011/0276098 | A1 * | 11/2011 | Biedermann | A61B 17/7037 606/305 |
| 2012/0109218 | A1 * | 5/2012 | Farris | 606/305 |
| 2012/0172932 | A1 * | 7/2012 | Biedermann et al. | 606/279 |
| 2012/0179209 | A1 * | 7/2012 | Biedermann et al. | 606/305 |
| 2012/0179211 | A1 * | 7/2012 | Biedermann et al. | 606/328 |
| 2012/0277805 | A1 * | 11/2012 | Farris | 606/305 |
| 2012/0283032 | A1 * | 11/2012 | Biedermann | A61B 17/7037 470/9 |
| 2013/0090693 | A1 * | 4/2013 | Strausbaugh et al. | 606/278 |
| 2014/0018859 | A1 * | 1/2014 | Biedermann et al. | 606/278 |
| 2015/0074977 | A1 * | 3/2015 | Biedermann | A61B 17/7037 29/453 |

FOREIGN PATENT DOCUMENTS

| | | |
|---|---|---|
| EP | 1923011 A1 | 5/2008 |
| JP | 2009-56292 A | 3/2009 |
| WO | WO 01/15612 A1 | 3/2001 |
| WO | WO 03/049629 A1 | 6/2003 |

* cited by examiner

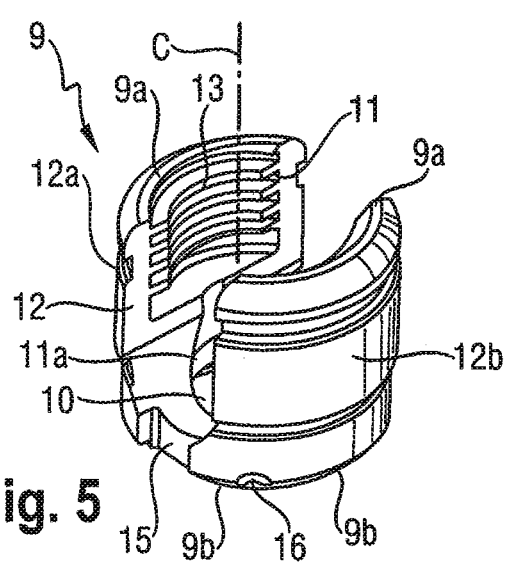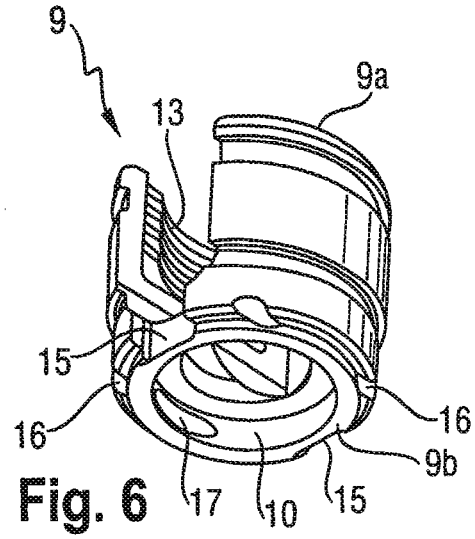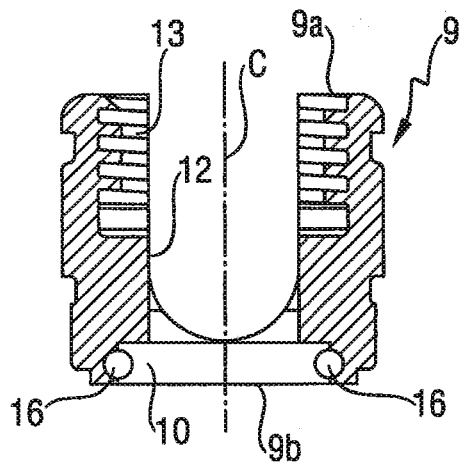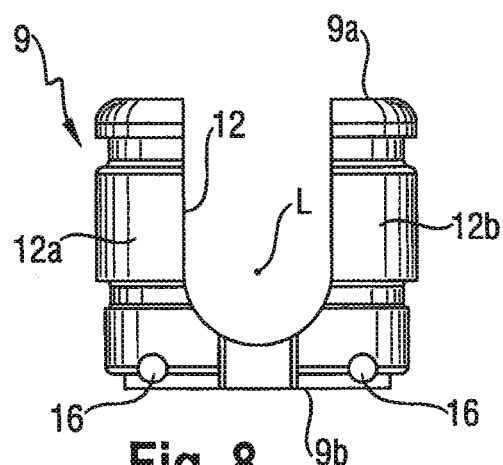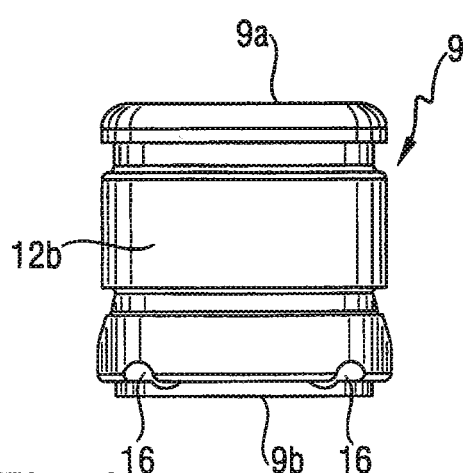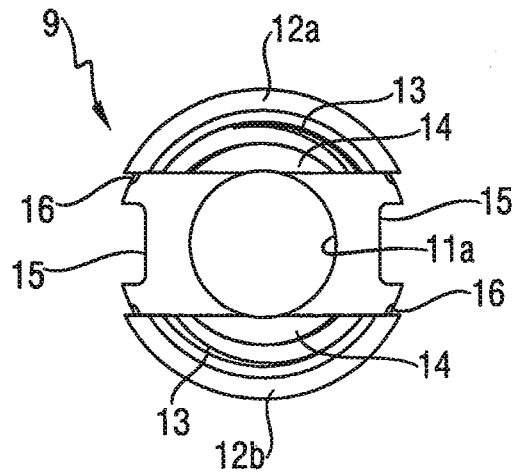

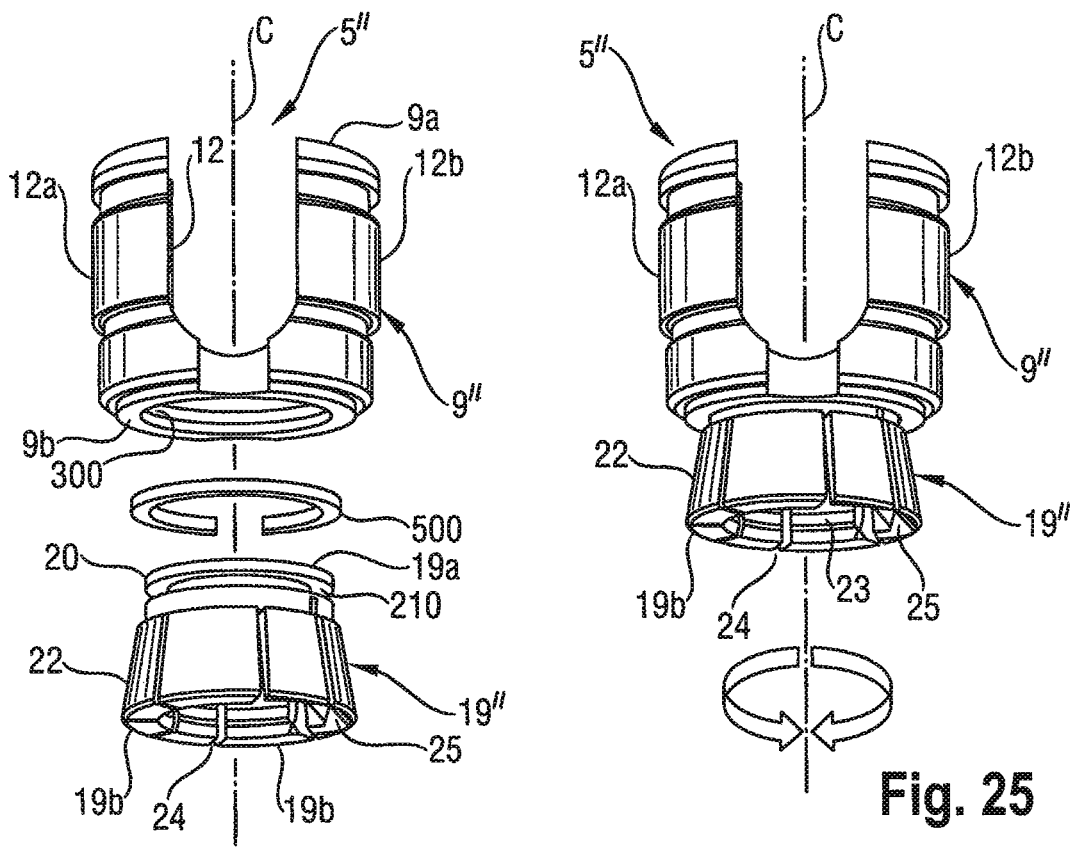
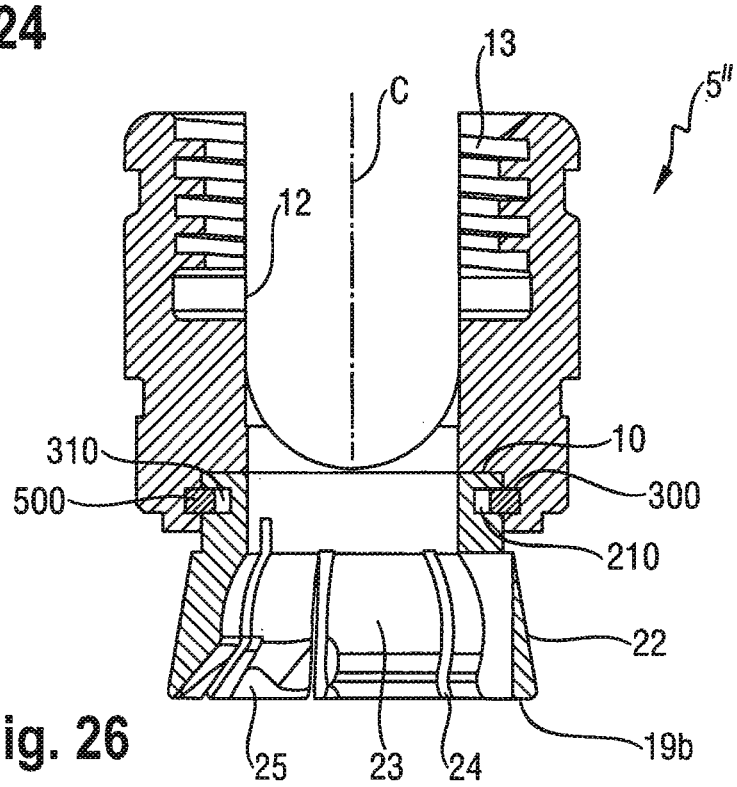
Fig. 24
Fig. 25
Fig. 26

POLYAXIAL BONE ANCHORING DEVICE WITH ENLARGED PIVOT ANGLE

CROSS-REFERENCE TO RELATED APPLICATION(S)

The present application claims the benefit of U.S. Provisional Patent Application Ser. No. 61/535,296, filed Sep. 15, 2011, the contents of which are hereby incorporated by reference in their entirety, and claims priority to European Patent Application EP 11 181 514.8, filed Sep. 15, 2011 the contents of which are hereby incorporated by reference in their entirety.

BACKGROUND

1. Field of the Invention

The invention relates to a polyaxial bone anchoring device with an enlarged pivot angle. The polyaxial bone anchoring device includes a bone anchoring element for anchoring in a bone and a receiving part for coupling a stabilization rod to the bone anchoring element. The receiving part includes a rod receiving portion for receiving the rod and a head receiving portion that is flexible so as to allow introduction and clamping of a head of the bone anchoring element. A locking ring is provided for compressing the head receiving portion of the receiving part to lock the head. A bounding edge of the head receiving portion is configured to permit the anchoring element to pivot at a larger pivot angle relative to the receiving part at a first location of the bounding edge than at a second location of the bounding edge. The head receiving portion is rotatable with respect to the rod receiving portion, so that an orientation or direction of the larger pivot angle can be selected.

2. Description of Related Art

A polyaxial bone anchoring device with an enlarged pivot angle is described in U.S. Pat. No. 6,736,820. This bone anchoring device includes a bone screw and a receiving part with a seat for the head of the bone screw. The screw member can be pivoted to at least one side by an enlarged angle, because the edge of the free end of the receiving part is of asymmetric construction.

Another polyaxial bone anchor is described in US 2005/0080415 A1. This bone anchor has a body member having a U-shaped channel for receiving the rod and a compressible recess for receiving a head of the anchor member such that the anchor member can initially polyaxially angulate with respect to the body member and further has a collar slidably disposed about the body member and capable of compressing the recess around the head. The lower bounding edge of the body member may include a countersunk region to permit increased angulation when the anchor member is oriented toward the countersunk region.

US 2007/0118123 A1 describes a polyaxial bone anchor with increased angulation. The polyaxial bone anchor has a locking element shaped and configured to allow an anchoring member, e.g. a screw or a hook, to polyaxially rotate at large angles about a central axis of the bone anchor before compression locking the anchoring member within an anchor head.

SUMMARY

Although the polyaxial bone anchoring devices described above provide for enlarged angulation in a specific orientation, there is still a need for an improved polyaxial bone anchoring device in terms of, for example, simplicity of design and increased variety of applications.

It is an object of the invention to provide a polyaxial bone anchoring device with an enlarged pivot angle that has a small size, provides for safer locking, and that in some embodiments, can be used as a modular system.

A polyaxial bone anchoring device according to embodiments of the invention is a bottom loading polyaxial bone anchoring device, where an anchoring element can be inserted into a receiving part from a bottom of the receiving part. In some embodiments, the bone anchoring device can be delivered by a manufacturer as a pre-assembled receiving part with locking ring, and separate therefrom, one or a plurality of different bone anchoring elements. By means of this, various bone anchoring elements with shanks having different diameters, thread forms and/or various other different features can be combined with the receiving part according to actual clinical requirements in a particular clinical situation. This gives the surgeon or other practioner a more diverse or wider choice of implants.

In addition, due to such modularity, costs of stock-holding can be decreased.

Because an enlarged pivot angle of bone anchoring devices according to embodiments of the invention can be selected for a range of 360° around a central axis of the receiving part, the bone anchoring device can be used in a wider variety of applications. A maximum pivot angle of the bone anchoring element relative to the receiving part may be equal to or greater than 45° measured from a straight position. An orientation or position of the enlarged pivot angle can be selected, for example, in a plane including the rod axis, at 90° with respect to the rod axis, or at any other angle. This renders the bone anchoring device according to embodiments of the invention particularly suitable for applications of lateral mass fixation, for example, at the cervical spine.

The design of the bone anchoring device according to embodiments of the invention provide for reduced dimensions in terms of height as well as in terms of diameter, which makes it particularly suitable for applications where small-sized anchoring devices are required, such as in the fields of cervical spine surgery or pediatric applications, trauma, and minimally open or minimally invasive applications for bone surgery.

BRIEF DESCRIPTION OF THE DRAWINGS

Further features and advantages will become apparent from the description of embodiments by means of accompanying drawings. In the drawings:

FIG. 5 shows a perspective view of a rod receiving portion of the receiving part of the polyaxial bone anchoring device of FIG. 1;

FIG. 6 shows a perspective view from below of the rod receiving portion of FIG. 5;

FIG. 7 shows a cross-sectional view of the rod receiving portion of FIGS. 5 and 6, the section taken perpendicular to the rod axis;

FIG. 8 shows a side view of the rod receiving portion of FIGS. 5 and 6;

FIG. 9 shows a side view of the rod receiving portion of FIG. 8 rotated by 90°;

FIG. 10 shows a top view of the rod receiving portion of FIGS. 5 and 6;

FIG. 24 shows a perspective exploded view of a receiving part of a polyaxial bone anchoring device without a locking ring, according to a third embodiment;

FIG. 25 shows a perspective view of the receiving part of FIG. 24 in an assembled state; and FIG. 26 shows a cross-sectional view of the receiving part of FIG. 24, the section taken perpendicular to a rod axis.

DETAILED DESCRIPTION

Figure 1:
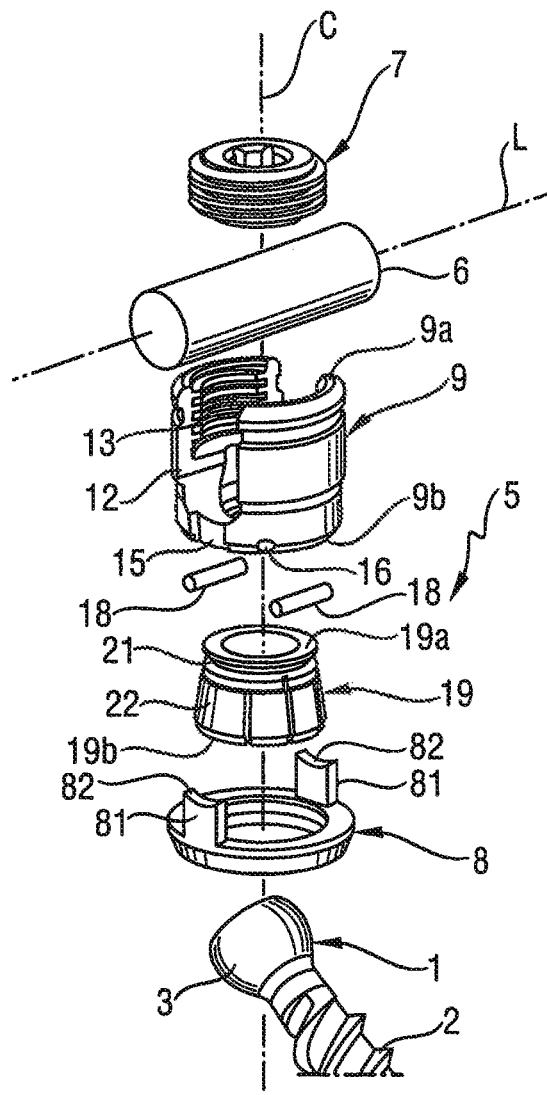
FIG. 1 shows an exploded perspective view of a polyaxial bone anchoring device according to a first embodiment.
Figure 2:
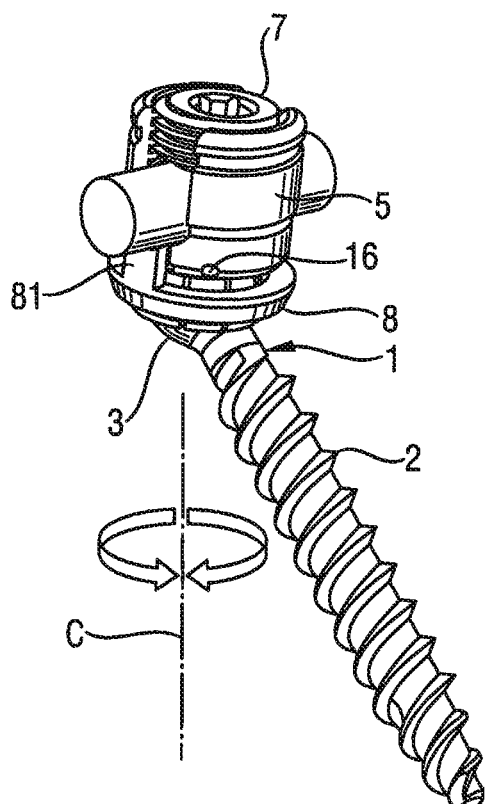
FIG. 2 shows a perspective view of the polyaxial bone anchoring device of FIG. 1 in an assembled state.

As shown in FIGS. 1 to 4, a polyaxial bone anchoring device according to a first embodiment includes a bone anchoring element 1 in the form of a bone screw having a threaded shank 2 and a spherical segment-shaped head 3. The head 3 has a recess 4 for engagement with a tool. The bone anchoring device further includes a receiving part 5 for receiving a rod 6 to connect the rod 6 to the bone anchoring element 1. Further, a closure element 7 in the form of, for example, an inner screw or set screw, is provided for securing the rod 6 in the receiving part 5. In addition, the bone anchoring device includes a locking ring 8 for locking the head 3 in the receiving part 5.

As can be further seen in FIGS. 1 to 16, the receiving part 5 includes a rod receiving portion 9 and a head receiving portion 19 that may be rotatably connected to each other. The rod receiving portion 9 is substantially cylindrical and has a first end 9a, an opposite second end 9b, and a central axis of symmetry C therethrough. The rod receiving portion 9 has a coaxial first bore 10 provided at the second end 9b. The rod receiving portion 9 also includes a coaxial second bore 11 extending from the first end 9a to a distance from the second end 9b, and a coaxial third bore 11a (see, e.g., FIG. 5) in communication with the first bore 10 and the second bore 11. A diameter of the second bore 11 is larger than a diameter of the rod 6. A substantially U-shaped recess 12 is provided in the rod receiving portion 9 that extends from the first end 9a towards the second end 9b, where a width of the U-shaped recess 12 is slightly larger than the diameter of the rod 6, to such an extent that the rod 6 can be placed in the recess 12 and can be guided therein. By means of the U-shaped recess 12, two free legs 12a, 12b are formed, on which an internal thread 13 is provided. The internal thread 13 can be, for example, a metric thread, a flat thread, a negative angle thread, a saw-tooth thread, or can have any other thread form. Preferably, a thread form such as a flat thread or a negative angle thread is used, which prevents splaying of the legs 12a, 12b when the inner screw 7 is screwed therein. A height of the U-shaped recess 12 is such that the rod 6 and the inner screw 7 can be inserted between the legs 12a, 12b. Between a bottom of the recess 12 and first end 9a along a longitudinal axis of the rod receiving portion 9, a flat section 14 is provided, forming or defining an end of the second bore 11 (see, e.g., FIG. 10).

At the second end 9b, two cut-outs 15 located diametrically opposite to each other are provided. The cut-outs 15 extend from the second end 9b into the bottom of the L-shaped recess 12. The cut-outs 15 are configured to receive a portion of the locking ring 8 described below.

On either side of the cut-outs 15, a pin hole 16 is provided that extends through the rod receiving portion 9 of the receiving part 5 to be parallel with a longitudinal axis L of a channel formed by the recess 12. The pin holes 16 each have a size such that the pin holes 16 project into or communicate with the first bore 10 along a circumferential length, thereby forming an opening 17, as shown in particular in FIG. 6. As depicted in FIGS. 1 to 4, two pins 18 are provided and are configured to be inserted into the pin holes 16, respectively. A length of the pins 18 is such that, in the inserted position, the pins 18 do not project out of an outer surface of the rod receiving portion 9 of the receiving part 5. When the pins 18 are inserted in the pin holes 16, a portion 18a of the pins 18 project through the opening 17 into the first bore 10, thereby reducing a diameter of the first bore 10 at the positions of the openings 17. The pins 18 may have a circular cross-section. The portions 18a that project through the openings 17 may have substantially a shape of an ellipse when viewed from the central axis C (see, e.g., FIG. 6).

The head receiving portion 19 of the receiving part 5 provides an accommodation space for the head 3 of the bone anchoring element 1. The head receiving portion 19 has a first end 19a configured to be connected to the second end 9b of the rod receiving portion 9, a second end 19b, and a coaxial through hole 19c. Adjacent to the first end 19a is a substantially cylindrical portion 20 with a circumferential groove 21. An outer diameter of the cylindrical portion 20 is the same as or is slightly smaller than the inner diameter of the first bore 10 of the rod receiving portion 9 of the receiving part 5, so that the cylindrical portion 20 fits into the first bore 10. A diameter of the groove 21 corresponds substantially to the inner diameter of the first bore 10 at the opening 17 when the pins 18 are inserted, as shown in particular in FIGS. 3 and 4.

The head receiving portion 19 further has a conically-shaped outer surface portion 22 that widens towards the second end 19b. In addition, an internal hollow spherical segment-shaped section 23 forming an accommodation space for the spherical segment-shaped head 3 of the bone anchoring element 1 is formed in the head receiving portion 19. The internal hollow section 23 is configured to encompass the head 3 of the bone anchoring element 1 from the side covering a region including a largest diameter of the head 3 when the head 3 is inserted therein.

As can be seen in particular in FIGS. 11 to 16, a plurality of slits 24 are provided that are open to the second end 19b of the head receiving portion 19. The slits 24 may end at a distance from the first end 19a. By the size and number of slits 24 provided, a desired elasticity is given to the head receiving portion 19. The elasticity of the head receiving portion 19 is such that the head 3 of the anchoring element 1 can be inserted by expanding the head receiving portion 19, and can be clamped in the head receiving portion 19 by compressing the head receiving portion 19.

An edge bounding the second end 19b may be asymmetric. In the embodiment shown, this is achieved by a countersunk or recessed area 25 at the internal hollow space 23. By means of this, the anchoring element 1 can pivot at the position of the recessed area 25 to a larger pivot angle $\alpha_1$ with respect to a straight position when an axis of the anchoring element 1 is coaxial with the central axis C of the receiving part 5 (see, e.g., FIG. 3), compared to a smaller pivot angle $\alpha_2$ in the opposite or other directions (see, e.g., FIG. 4). The recessed area 25, therefore, defines a position for facilitating an enlarged pivot angle of the anchoring element 1 with respect to the rod receiving portion 9.

Figure 17:
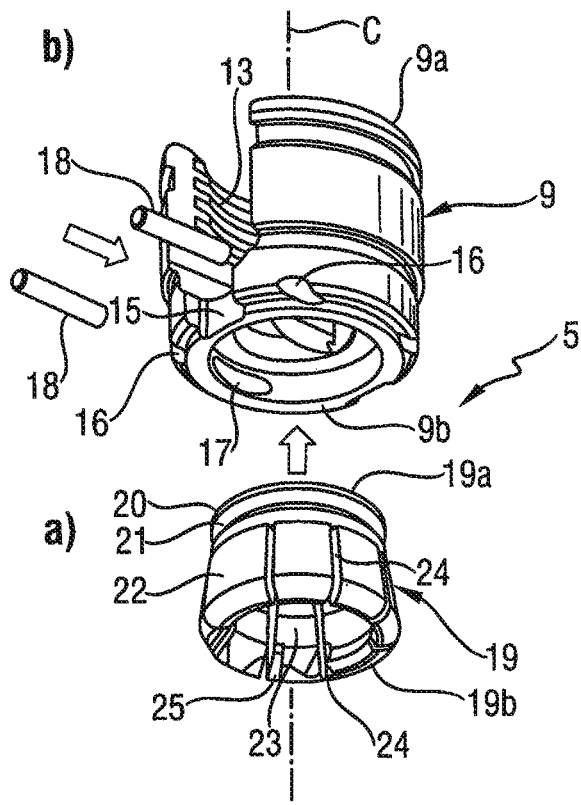
FIG. 17 shows an exploded perspective view of a receiving part according to an embodiment, without a locking ring, and showing steps of assembly.
Figure 18:
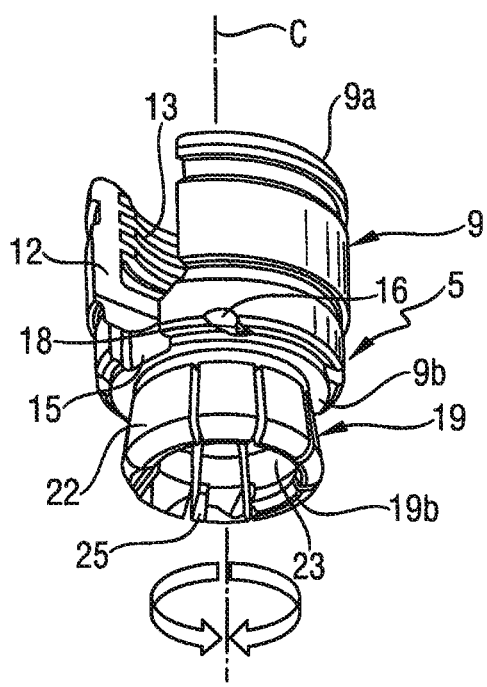
FIG. 18 shows a perspective view of an assembled rod receiving portion and head receiving portion of the receiving part of FIG. 17.

The receiving part 5 is assembled as shown in FIGS. 17 and 18. In a first step, the head receiving portion 19 is introduced into the rod receiving portion 9 from the second end 9b of the rod receiving portion 9, until the first end 19a abuts an end of the first bore 10 (See, e.g., FIGS. 3 and 4). Then, in a second step, the pins 18 are introduced into the pin holes 16 so that they extend partially through the openings 17 into the groove 21. By means of this, the head receiving portion 19 is connected to the rod receiving portion 9 so that it cannot fall out. The pins 18 extend through the openings 17 such that the pins 18 are able to move in or with respect to the groove 21. This renders the head receiving portion 19 rotatable with respect to the rod receiving portion 9. As such, an orientation or position of the recessed area 25 with respect to an orientation or position of an axis of an inserted rod can be selected or adjusted to any angle between zero and 360° by rotating the head receiving portion 19 with respect to the rod receiving portion 9 in, for example, a clockwise or counterclockwise direction.

Figure 3:
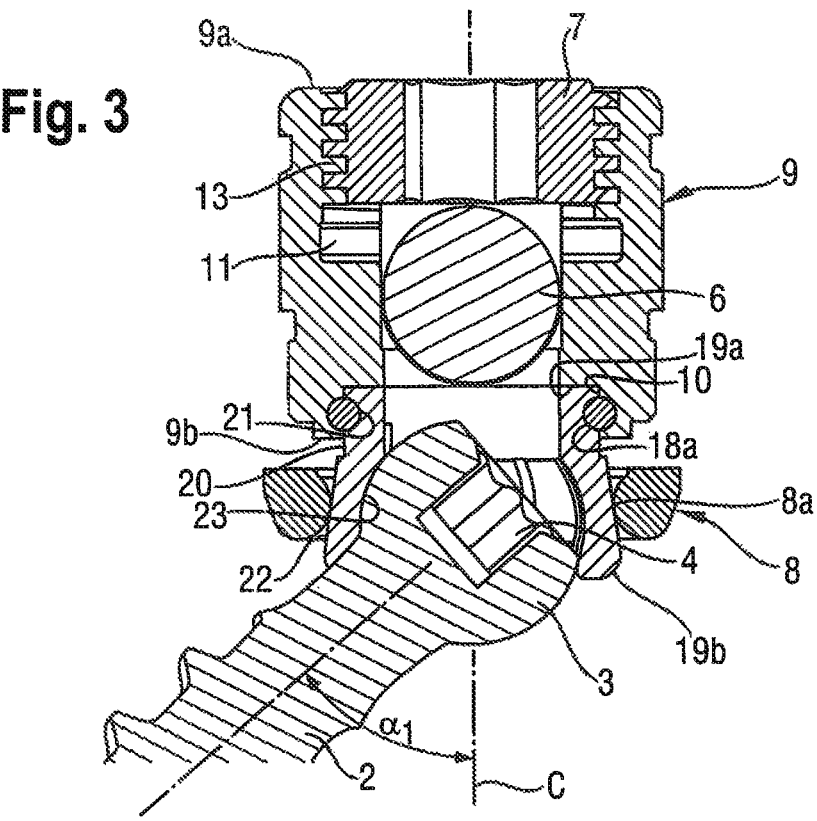
FIG. 3 shows a cross-sectional view of the polyaxial bone anchoring device of FIGS. 1 and 2, the section taken perpendicular to a rod axis, where a bone anchoring element is in a first pivot position.
Figure 4:
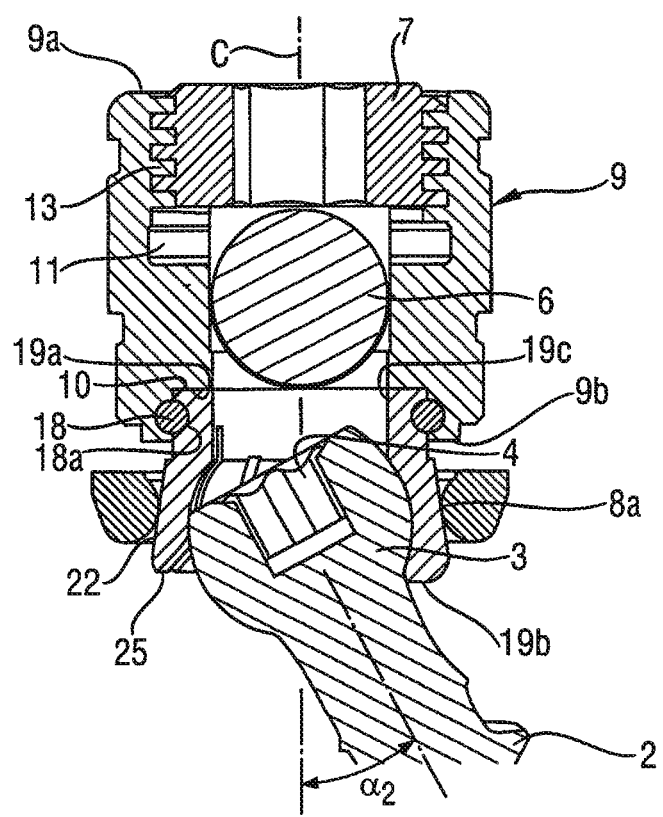
FIG. 4 shows a cross-sectional view of the polyaxial bone anchoring device of FIGS. 1 and 2, the section taken perpendicular to the rod axis, where the bone anchoring element is in a second pivot position.
Figure 11:
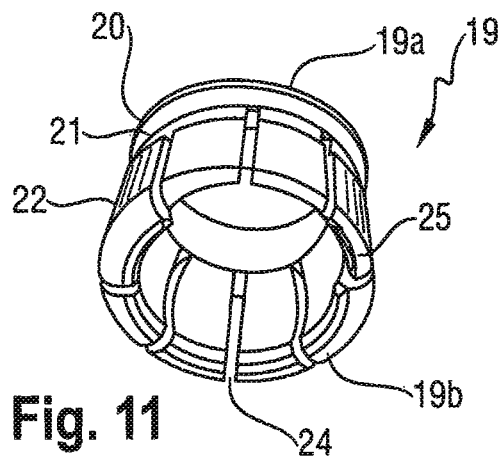
FIG. 11 shows a perspective view from below of a head receiving portion of the receiving part of the polyaxial bone anchoring device of FIG. 1.
Figure 12:
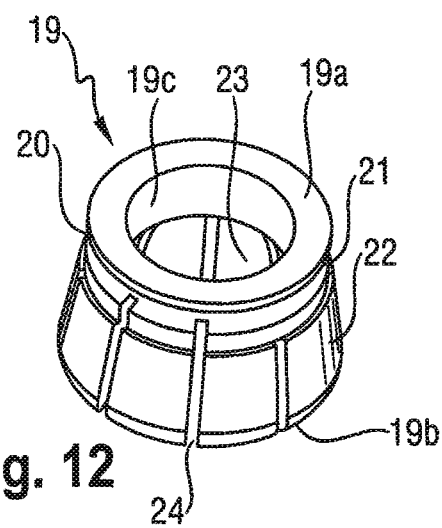
FIG. 12 shows a perspective view from above of the head receiving portion of FIG. 11.
Figure 13:
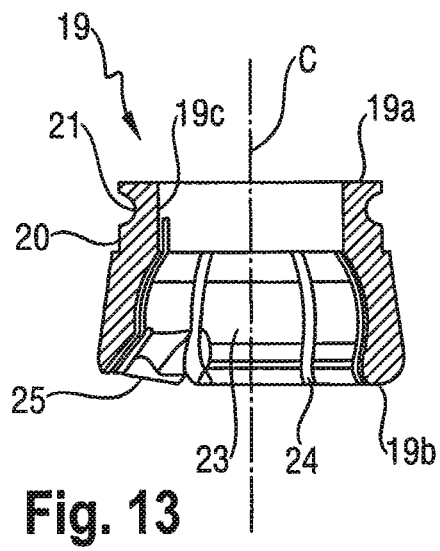
FIG. 13 shows a cross-sectional view of the head receiving portion of FIGS. 11 and 12.
Figure 14:
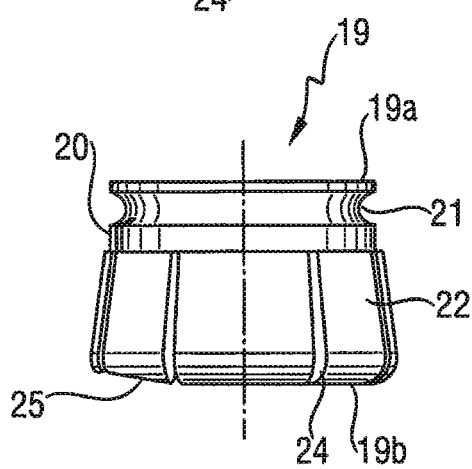
FIG. 14 shows a side view of the head receiving portion of FIGS. 11 and 12.
Figure 15:
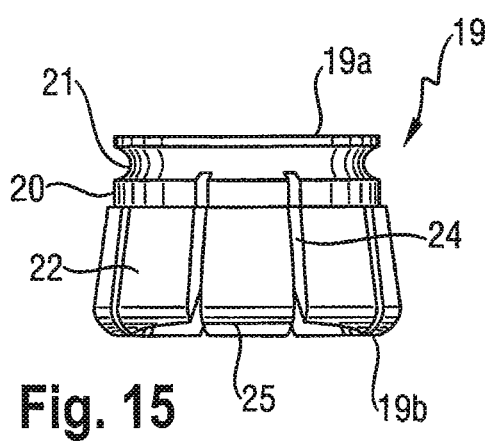
FIG. 15 shows a side view of the head receiving portion of FIG. 14 rotated by 90°.
Figure 16:
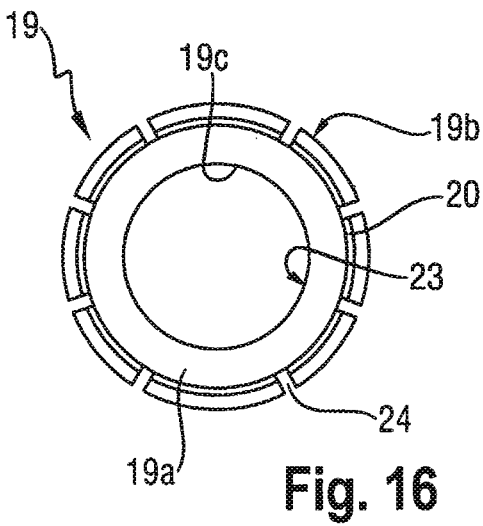
FIG. 16 shows a view from a top of the head receiving part of FIGS. 11 and 12.
Figure 19:
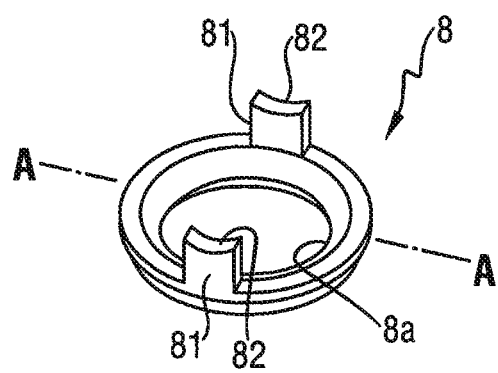
FIG. 19 shows a perspective view of a locking ring according to an embodiment.
Figure 20:
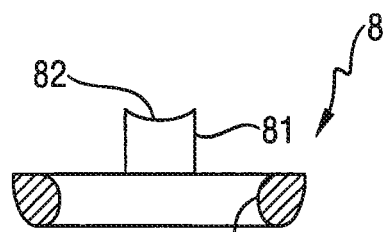
FIG. 20 shows a cross-sectional view of the locking ring of FIG. 19, the section taken along line A-A in FIG. 19.

The locking ring 8 will now be described with reference to FIGS. 19 and 20. The locking ring 8 has a maximum outer diameter that does not project or only slightly projects outward from an outer surface of the rod receiving portion 9 of the receiving part 5 when the locking ring 8 is mounted on the receiving part 5. A height of the locking ring 8 in an axial direction (not taking into consideration projections 81, discussed further below) is smaller than that of the head receiving portion 19 of the receiving part 5 so that, as shown in FIGS. 3 and 4, there is a distance or gap between the locking ring 8 and the second end 9b of the rod receiving portion 9 when the locking ring 8 is in a position for clamping the head 3.

The locking ring 8 has at its inner side a curved internal surface portion 8a. A curvature of the inner surface portion 8a is directed towards a center of the locking ring 8. The curved surface portion 8a may have a circular segment-shaped cross section. Other types of curvatures are also possible. An inner diameter of the locking ring 8 is such that the locking ring 8 can slide along the outer conical surface portion 22 of the head receiving portion 19, thereby compressing the head receiving portion 19 increasingly when sliding downwards (i.e., towards second end 19b).

Furthermore, the locking ring 8 includes two projections 81 located diametrically opposite to each other on a side that faces the second end 9b of the rod receiving portion 9 when the locking ring 8 is mounted. The projections 81 have a height such that they extend into the cut-outs 15 and project above the bottom of the substantially U-shaped recess 12 when the locking ring 8 is in a position in which an inserted head 3 is not yet clamped. Free ends 82 of the projections 81 can be curved, particularly concavely curved with a curvature that may correspond to that of the rod 6. The locking ring 8 is arranged in such a way around the head receiving portion 19 of the receiving part 5 that the projections 81 are located at the positions of the recess 12. By means of this, the projections 81 that project through the cut-outs 15 into the recess 12 prevent the locking ring 8 from rotating out of this position when the rod 6 is not yet inserted.

The locking ring 8 is mounted from the second end 19b of the head receiving portion 19. When the locking ring 8 is in an uppermost position abutting against the second end 9b of the rod receiving portion 9, the head receiving portion 19 is still freely rotatable with respect to the rod receiving portion 9.

The flexibility of the head receiving portion 19 and the size of the head receiving portion 19 at the open second end 19b allows for mounting of the locking ring 8 by assembling the locking ring 8 from the second end 19b onto the head receiving portion 19. Because the outer diameter of the head receiving portion 19 is smaller than that of the rod receiving portion 9, the locking ring 8 may not project or only minimally projects beyond the rod receiving portion 9 in a radial direction when mounted.

The locking ring 8 is moveable between a first position limited by the second end 9b of the rod receiving portion 9 of the receiving part 5 that acts as a stop, and a second position near the second end 19b of the head receiving portion 19. In the second position, the head 3 is locked by means of compression of the head receiving portion 19. The tapered exterior surface 22 of the head receiving portion 19 prevents escaping of the locking ring 8 in the direction of the second end 19b when the head 3 is inserted in the head receiving portion 19.

The inner screw 7 has a thread corresponding to the internal thread 13 provided on the legs 12a, 12b. If a thread form that prevents the legs 12a, 12b from splaying is used, a single closure element such as the inner screw 7 may be sufficient. This reduces a size of the bone anchoring device in a radial direction.

The receiving part 5, the locking ring 8, the inner screw 7 and the bone anchoring element 1 may be made of bio-compatible materials, for example, of titanium or stainless steel, of bio-compatible alloys, such as nickel titanium alloys, for example Nitinol, or of a bio-compatible plastic material, such as, for example, polyetheretherketone (PEEK). The various parts can be made of the same or of different materials.

The bone anchoring device according to embodiments of the invention can be used in several ways. In one way of use, the bone anchoring element 1, the receiving part 5, and the locking ring 8 may be pre-assembled. The head receiving portion 19 of the receiving part 5 is rotated to a desired position such that the recessed area 25 that defines the orientation or position of the enlarged pivot angle is positioned at a desired orientation. The bone anchoring element 1 is inserted into a bone with the receiving part 5 mounted on the bone anchoring element 1. The recess 4 of the head can be accessed with a tool through the first, second and third bores 10, 11, and 11*a*. The locking ring 8 may be in a first position close to the second end 9*b* of the rod receiving portion 9, where the locking ring 8 does not yet facilitate clamping of the head 3. The flexible head receiving portion 19 of the receiving part 5 may create a slight pretension, where the inner surface of the hollow portion 23 may be slightly smaller in dimension than the head 3. Therefore, the receiving part 5 may be frictionally held on the head 3 in a specific angular position. The receiving part 5 can then be aligned manually to receive the rod 6. Once a correct position of the rod 6 with respect to each of the bone anchoring devices is achieved, the inner screw 7 is screwed between the legs 12*a*, 12*b* until the inner screw 7 presses onto the rod 6. The rod 6 is pressed into or towards the bottom of the U-shaped recess 12, thereby engaging the free ends 82 of the projections 81, respectively, and shifting down the locking ring 8. When the locking ring 8 is moved towards the second end 19*b* of the head receiving portion 19, the locking ring 8 compresses the head receiving portion 19 and clamps the head 3. Final tightening of the inner screw 7 locks positions of the rod 6 and the head 3 relative to the receiving part 5 simultaneously.

In another way of use, only the receiving part 5 and the locking ring 8 may be pre-assembled. An appropriate bone anchoring element may be selected from a variety of bone anchoring elements and introduced into the hollow internal portion 23 while the locking ring 8 is at a position close to the second end 9*b* of the rod receiving portion 9. This allows for selection of an appropriate bone anchoring element out of a variety of bone anchoring elements that may, for example differ in diameter, length, and/or other features or properties. Hence, a modular system may be provided, including receiving parts and a plurality of bone anchoring elements which can then be individually selected. It may also be possible to provide a plurality of receiving parts with, for example, differently shaped or configured recessed areas to accommodate a wider variety of enlarged pivot angles. By means of such modularity, the fields of application of the bone anchoring device according to embodiments of the invention may be enlarged.

In yet another way of use the inner screw 7 may be tightened to lock the head 3 and the rod 6. Thereafter, the inner screw 7 may be loosened to allow further adjustments of the rod 6. The head 3 may remain temporarily clamped due to a frictional force or other feature that holds the locking ring 8 in place.

Figure 21:
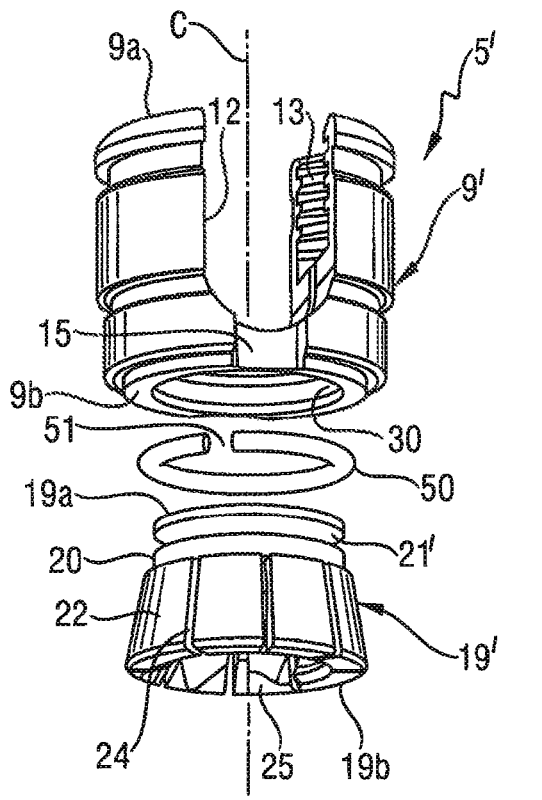
FIG. 21 shows an exploded perspective view of a receiving part of a polyaxial bone anchoring device, without a locking ring, according to a second embodiment.
Figure 22:
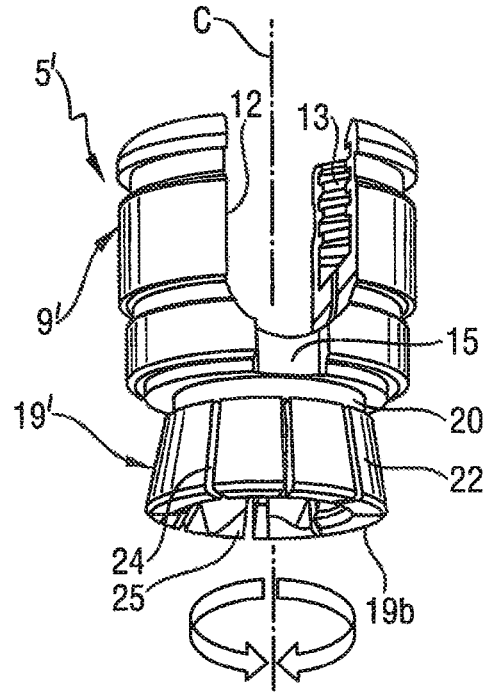
FIG. 22 shows a perspective view of the receiving part of FIG. 21 in an assembled state.
Figure 23:
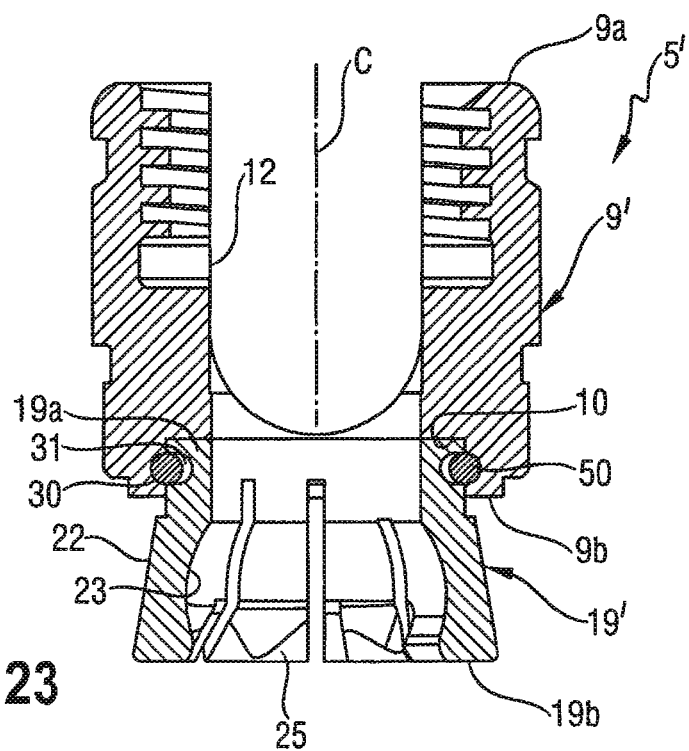
FIG. 23 shows a cross-sectional view of the assembled receiving part of FIGS. 21 and 22 the section taken perpendicular to a rod axis.

FIGS. 21 to 23 show a second embodiment of a polyaxial bone anchoring device that differs from the first embodiment by the receiving part. The receiving part 5' according to the second embodiment includes a rod receiving portion 9' for receiving the rod 6 and a head receiving portion 19' for receiving the head 3 of the bone anchoring element 1. Portions and sub-portions that are identical or similar to those of the first embodiment are indicated with the same reference numerals, and the descriptions thereof will not be repeated. The rod receiving portion 9' does not have pin holes 16, and the pins 18 are not implemented. The rod receiving portion 9' instead has a circumferential groove 30 at a distance from the second end 9*b*. The head receiving portion 19' has near the first end 19*a* a circumferential groove 21' for accommodating a split ring 50. The split ring 50 is a ring with a circular cross section that substantially corresponds to a cross section of the groove 30 and that is open, or in other words, has a gap 51. Therefore, the split ring 50 exhibits flexibility. A size of the split ring 50 is such that if the gap 51 is closed by compressing the split ring 50, the split ring 50 may be contained fully within the groove 21'. The grooves 21' and 30 are configured to face each other when the head receiving portion 19' is inserted into the rod receiving portion 9'. The sizes of the grooves 21', 30 are such that, when the grooves 21', 30 face each other, there is a space 31 allowing the split ring 50 to expand and compress therein.

Assembly of the receiving part 5' according to the second embodiment is as follows. First, the split ring 50 is expanded and inserted into the groove 21' of the head receiving portion 19'. Then, the head receiving portion 19' together with the split ring 50 (which may temporarily be compressed in the groove 21' during connection of the rod receiving portion 9' and the head receiving portion 19') is inserted from the second end 9*b* into the rod receiving portion 9'. When the first end 19*a* abuts against the end of the first bore 10, the grooves 21', 30 face each other, and the split ring 50 expands. By means of this, the head receiving portion 19' may be prevented from falling out. Meanwhile, the head receiving portion 19' may still be rotatable with respect to rod receiving portion 9', to allow the recessed area 25 to be rotated to a desired position relative to the rod receiving portion 9'.

In an alternate approach, the split ring 50 can first be compressed for insertion into the first bore 10 of the rod receiving portion 9', and then allowed to expand into groove 30. Thereafter, the head receiving portion 19' can be inserted from the second end 9*b* into the rod receiving portion 9'. Here, a space similar to space 31 may be arranged in the rod receiving portion 9' to allow for further expansion of the split ring 50 in the groove 30 when the head receiving portion 19' is inserted into the rod receiving portion 9'. When the first end 19*a* of the head receiving portion 19' abuts against the end of the first bore 10, the grooves 21', 30 face each other, and the split ring 50 can compress into the groove 21 to prevent the head receiving portion 19' from falling out of the first bore 10 and separating from the rod receiving portion 9.

The mounting of the locking ring 8 and the assembly of the whole anchoring device may be the same as or similar to the first embodiment.

A third embodiment of the polyaxial bone anchoring device is shown in FIGS. 24 to 26. The third embodiment differs in the design of the receiving part 5'' and the split ring 500 from the second embodiment. Portions and sub-portions that are the same as or similar to those of the first and/or second embodiments are indicated with the same reference numerals, and the descriptions thereof will not be repeated.

The third embodiment has a split ring 500 with a rectangular cross section. Also, a groove 300 in the rod receiving portion 9''' and a groove 210 in the head receiving portion 19''' have rectangular cross sections, with respective long sides perpendicular to the central axis C. The rectangular cross-sections may provide for more secure abutting surfaces and/or a stronger holding force compared to the second embodiment.

Assembly and use of the bone anchoring device according to the third embodiment is similar to the assembly and use of the polyaxial bone anchoring device according to the first and the second embodiments. For example, the split ring 500 is inserted into the groove 210 and compressed during insertion, or can alternatively be inserted into the groove 300 and expanded during insertion, similarly as described for the second embodiment.

When the head receiving portion 19″ is mounted to the rod receiving portion 9″, the split ring 500 is configured to expand into the groove 300 because the dimensions of the grooves 210, 300 are such that there is a gap 310 provided when the grooves 210, 300 are aligned. Due to the rectangular cross-sections of the split ring 500 and the grooves 210 and 300, a greater friction force may be provided such that, during rotation of the head receiving portion 19″, a more precise adjustment of a position of the recessed area 25 relative to the rod receiving portion 9″.

Further modifications of the embodiments described may also be conceivable. For example, for the bone anchoring element, various different kinds of anchoring elements can be used and combined with the described receiving parts. Such anchoring elements may include, for example, screws of different lengths, screws with different diameters, cannulated screws, screws with different thread forms, nails, hooks, etc. In some embodiments, the head and the shank of the anchoring elements may be separate parts that are connectable to each other.

Modifications of the receiving part are also possible. For example, to generate the enlarged pivot angle, it is possible to use a head receiving portion that has been cut at the bottom in an inclined manner so as to generate an enlarged pivot angle over a larger circumferential area. The recessed area can also be realized by a cut-out in an otherwise symmetric head receiving portion that provides an opening perpendicular to the central axis C.

Rotational support of the head receiving portion in the rod receiving portion can also be realized in other ways. For example, the pins in the first embodiment and the corresponding pin holes can be placed at other locations in the circumferential direction. In some embodiments, one single pin hole and a single pin may be sufficient. Further, instead of the pins or the split ring, for example, it may also be possible to use, for example, a slotted ring with alternating slots, or one or more ball bearings. The connection between the rod receiving portion and the head receiving portion is generally at least partially a positive-fit connection. However, it is also conceivable to have a connection that is achieved by a friction-fit only.

A configuration of the locking ring and the cooperating outer surface portion of the head receiving portion can also be different from the embodiments shown. For example, it is possible for the inner surface of the locking ring to also be tapered and to cooperate with the tapered outer surface of the head receiving portion. The cooperating surfaces of locking ring and head receiving portion can also be parallel (e.g., with the central axis of the receiving part) so that the clamping of the head is achieved by an interference fit between the locking ring and the head receiving portion. Any other configuration that generates a sufficient locking force for locking the head may be conceivable.

Further, in some embodiments, instead of the U-shaped recess for receiving the rod, a recess that is open to the side can be used, or the channel for the rod may be closed. Other kinds of locking or fixation devices, including outer nuts, outer caps, bayonet locking devices, or other similar fixation devices may also be incorporated are possible.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
   a bone anchoring element having a shank for anchoring in a bone and a head;
   a receiving part for coupling a rod to the bone anchoring element, the receiving part comprising:
      a rod receiving portion having a first end, a second end, and a recess with a bottom for receiving a rod therein; and
      a head receiving portion having a first end, an open second end with a bounding edge, and a hollow interior portion in communication with the second end for accommodating the head of the bone anchoring element, wherein a first region of the head receiving portion is insertable into the second end of the rod receiving portion to rotatably connect the head receiving portion to the rod receiving portion, and wherein the head receiving portion is flexible for introduction and clamping of the head; and
   a locking ring configured to be mounted around the head receiving portion;
   wherein when the head receiving portion is connected to the rod receiving portion and the locking ring is around the head receiving portion, the head is insertable into the head receiving portion from the second end of the head receiving portion, is pivotable in the head receiving portion such that the bounding edge is configured to permit the bone anchoring element to pivot at a larger maximum pivot angle relative to the receiving part at a first location of the bounding edge than at a second location of the bounding edge, and can be locked at an angle relative to the receiving part by compressing the head receiving portion with the locking ring; and
   wherein when the first region of the head receiving portion is in the rod receiving portion, at least one retaining element is insertable into the receiving part to connect the head receiving portion to the rod receiving portion.

2. The polyaxial bone anchoring device of claim 1, wherein the first end of the head receiving portion is configured to be connected to the second end of the rod receiving portion.

3. The polyaxial bone anchoring device of claim 1, wherein the head receiving portion and the rod receiving portion are configured to be connected by a positive-fit connection.

4. The polyaxial bone anchoring device of claim 1, wherein the first end of the head receiving portion comprises a cylindrical portion and the second end of the rod receiving portion has a bore into which the cylindrical portion fits.

5. The polyaxial bone anchoring device of claim 4, wherein the cylindrical portion of the head receiving portion has a circumferential groove.

6. The polyaxial bone anchoring device of claim 5, wherein the rod receiving portion has at least one pin hole, and wherein the at least one retaining element comprises a pin configured to be positioned in the pin hole so as to extend at least partially into the groove when the head receiving portion and the rod receiving portion are connected.

7. The polyaxial bone anchoring device of claim 1, wherein the bounding edge comprises a recessed area at the first location that provides for the larger maximum pivot angle.

8. The polyaxial bone anchoring device of claim 1, wherein when the locking ring compresses the head receiving portion to lock the head, an orientation of the head receiving portion is fixed with respect to the rod receiving portion.

9. The polyaxial bone anchoring device of claim 1, wherein when the rod receiving portion and the head receiving portion are connected, the receiving part has a central axis that extends from the first end of the rod receiving portion to the second end of the head receiving portion, and wherein the locking ring is configured to be movable along the central axis.

10. The polyaxial bone anchoring device of claim 1, further comprising a rod, wherein the locking ring is moveable by exerting pressure onto the locking ring with the rod to compress the head receiving portion and lock the head.

11. The polyaxial bone anchoring device of claim 1, wherein the recess for the rod is a U-shaped recess.

12. The polyaxial bone anchoring device of claim 1, wherein the locking ring is mountable from the second end of the head receiving portion.

13. The polyaxial bone anchoring device of claim 1, wherein the head receiving portion further defines an open first end with a width that is less than a greatest width of the head of the bone anchoring element.

14. The polyaxial bone anchoring device of claim 1, wherein the at least one retaining element is a pin, the rod receiving portion has at least one pin hole, and wherein the pin is configured to be inserted in the pin hole to connect the head receiving portion to the rod receiving portion.

15. The polyaxial bone anchoring device of claim 1, wherein the rod receiving portion comprises a connection region between the bottom of the recess and the second end; and Wherein when the head receiving portion is connected to the rod receiving portion and the locking ring is around the head receiving portion, a greatest width of the head receiving portion is less than a width of an outer profile of the rod receiving portion at the connection region.

16. The polyaxial bone anchoring device of claim 1, wherein when the locking ring is mounted around the head receiving portion, the second end of the rod receiving portion forms an abutment for the locking ring.

* * * * *

UNITED STATES PATENT AND TRADEMARK OFFICE
CERTIFICATE OF CORRECTION

PATENT NO.        : 9,452,006 B2
APPLICATION NO. : 13/610045
DATED             : September 27, 2016
INVENTOR(S)       : Biedermann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this
Twenty-fifth Day of September, 2018

Andrei Iancu
*Director of the United States Patent and Trademark Office*